US005776958A

United States Patent [19]
Warrellow et al.

[11] Patent Number: 5,776,958
[45] Date of Patent: *Jul. 7, 1998

[54] TRISUBSTITUTED PHENYL DERIVATIVES AND PROCESSES FOR THEIR PREPARATION

[75] Inventors: Graham John Warrellow, Northwood; Ewan Campbell Boyd, Tullibody; Rikki Peter Alexander, High Wycombe; Michael Anthony William Eaton, Watlington, all of United Kingdom

[73] Assignee: Celltech Therapeutics, Limited, Slough, United Kingdom

[*] Notice: The terminal 14 months of this patent has been disclaimed.

[21] Appl. No.: 360,563

[22] Filed: Dec. 21, 1994

[30] Foreign Application Priority Data

Dec. 22, 1993 [GB] United Kingdom ............... 9326600

[51] Int. Cl.$^6$ .......................... A61K 31/44; C07D 211/86
[52] U.S. Cl. .................. 514/345; 546/290; 546/268.1; 546/216; 546/207; 514/327; 514/326; 514/317
[58] Field of Search ............................ 546/290, 268.1, 546/216, 207; 514/345, 327, 326, 317

[56] References Cited

U.S. PATENT DOCUMENTS

| | | | |
|---|---|---|---|
| 4,788,195 | 11/1988 | Torley et al. | 514/252 |
| 4,876,252 | 10/1989 | Torley et al. | 514/224.8 |
| 4,897,396 | 1/1990 | Hubele | 514/275 |
| 4,966,622 | 10/1990 | Rempfler et al. | 71/92 |
| 5,159,078 | 10/1992 | Rempfler et al. | 544/330 |
| 5,340,827 | 8/1994 | Beeley et al | 514/352 |
| 5,491,147 | 2/1996 | Boyd et al | 514/247 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow | 514/336 |
| 5,693,659 | 12/1997 | Head et al. | 514/357 |

FOREIGN PATENT DOCUMENTS

| | | |
|---|---|---|
| 0233461A2 | 8/1987 | European Pat. Off. . |
| 0295210A1 | 12/1988 | European Pat. Off. . |
| 0337943A2 | 10/1989 | European Pat. Off. . |
| 0564409A1 | 10/1993 | European Pat. Off. . |
| 2 545 356 A1 | 11/1984 | France . |
| 3-77872 | 4/1991 | Japan . |
| 3-77923 | 4/1991 | Japan . |
| WO 93/100118 | 5/1993 | WIPO . |
| WO 94/10118 | 5/1994 | WIPO . |
| WO 94/13661 | 6/1994 | WIPO . |
| WO 94/14742 | 7/1994 | WIPO . |
| WO 94/20446 | 9/1994 | WIPO . |
| WO 94/20455 | 9/1994 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 95/17386 | 6/1995 | WIPO . |
| WO 95/31451 | 11/1995 | WIPO . |
| WO 95/33727 | 12/1995 | WIPO . |
| WO 96/14843 | 5/1996 | WIPO . |

OTHER PUBLICATIONS

Trost and Fleming (eds.), Comprehensive Organic Synthesis, Pergamon Press, New York, 1991, 3, 531–541.

Vidal et al., "Electrophilic Amination: Preparation and Use of N–Boc–3–(4–cyanophenyl)oxaziridine, a New Reagent That Transfers a N–Boc Group to N–and C–Nucleophiles", J. Org. Chem., 1993, 58, 4791–4793.

Chemical Abstracts, "Hypoglycemic Pharmaceuticals Containing Manzammide Derivatives", Chem. Abstr. , 1983, 99 (6), No. 43558Z.

(List continued on next page.)

*Primary Examiner*—C. Warren Ivy
*Assistant Examiner*—Charanjit S. Aulakh
*Attorney, Agent, or Firm*—Woodcock Washburn Kurtz MacKiewicz & Norris, LLP

[57] ABSTRACT

Compounds of general formula (1):

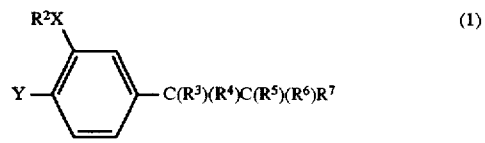

(1)

wherein

Y is a halogen atom or a group —$OR^1$ where $R^1$ is an optionally substituted alkyl group;

X is —O—, —S— or —$N(R^8)$—, where $R^8$ is a hydrogen atom or an alkyl group;

$R^2$ is an optionally substituted alkyl, alkenyl, cycloalkyl or cycloalkenyl group;

$R^3$ is a hydrogen or halogen atom or an —$OR^9$ group, where $R^9$ is a hydrogen atom or an optionally substituted alkyl, alkenyl, alkoxyalkyl, or alkanoyl group, or a formyl, carboxamido or thiocarboxamido group;

$R^4$ is a group —$(CH_2)_n Ar$, where Ar is a monocyclic or bicyclic aryl group optionally containing one or more heteroatoms selected from oxygen, sulphur or nitrogen atoms and n is zero or an integer 1,2 or 3;

$R^5$ is a $C_{3-9}$ carbocyclic ketone optionally containing one or more heteroatoms selected from oxygen, sulphur or nitrogen atoms;

$R^6$ is a hydrogen atom or an optionally substituted alkyl group;

$R^7$ is a hydrogen atom or an optionally substituted alkyl group; and the salts, solvates, hydrates and N-oxides thereof.

Compounds according to the invention are potent and selective phosphodiesterase type IV inhibitors and are useful in the prophylaxis and treatment of diseases such as asthma where an unwanted inflammatory response or muscular spasm is present.

24 Claims, No Drawings

OTHER PUBLICATIONS

Dent et al., "Inhibition of eosinophil cyclic nucleotide PDE activity and opsonised zymosan–stimulated respiratory burst by type IV'–selective PDE inhibitors", *Br. J. Pharmacol.*, 1991, 103, 1339–1346.

Grammaticakis, "Contribution A L'Etude de L'Absortion Dans L'Ultraviolet Moyen Et Le Visible Des N–Aroyl–Arylamines. IV. 2 , 3–, 3 , 4–et 2 , 4–, dimethoxybenzoylarylamines", *Bullentin DeLa Societa Chemique De France*, 1965, 848–858.

Green and Wuts, "Protective Groups in Organic Synthesis", John Wiley & Sons, New York, 1991.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 88–896.

Karlsson et al., "T–Lymphocyte and Inflammatory Cell Research in Asthma", Joller, G. et al. (eds.), Academic Press, 1993, 323–347.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Shioiri et al., "New Methods and Reagents in Organic Synthesis. 3. Diethyl Phosphorocyanidate: A New Reagent for C–Acylation", *J. Org. Chem.*, 1978, 43, 3631–3632.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo [3, 4–d ]pyrimidines, and 5–Aza [2 . 2 . 3 ]cyclazines", *J. Het. Chem.*, 1990, 27, 647–660.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Daves, G.D. et al., "Pyrimidines. XIII. 2–and 6–Substituted 4 –Pyrimidinecarboxylic Acids", *J. Of Hev. Chem.*, 1964, 1, 130–133.

Dietl, F. et al., "Chinone von Benzo–und Dibenzokronenethern", *Synthesis*, 1985, 626–631.

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Hanks S.K. et al., "The eukaryotic protein kinase superfamily: kinase (catalytic) domain structure and classification", *FASEB J.*, 1995, 9, 576–596.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Newton, A.C., "Protein Kinase C: Structure, Function, Regulation", *J. Biol. Chem.*, 1995, 270(48), 28495–28498.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", TIBS, 1993, 18, 195–197.

Plé, N. et al., "Metalation of Diazines. XI. Directed Ortho–Lithiation of Fluoropyrimidines and Application to Synthesis of an Azacarboline", *J. Heterocylic Chem.*, 1994, 31, 1311–1315.

Sánchez, H.I. et al., "Formal Total Synthesis of β–Pipitzol", *Tetrahedron*, 1985, 41 (12) , 2355–2359.

TRISUBSTITUTED PHENYL DERIVATIVES AND PROCESSES FOR THEIR PREPARATION

This invention relates to a novel series of tri-substituted phenyl derivatives, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenylyl cyclase which may be directly activated by agents such as forskolin or indirectly activated by the binding of specific agonists to cell surface receptors which are coupled to adenylyl cyclase. The breakdown of cAMP is controlled by a family of phosphodiesterase (PDE) isoenzymes, which also control the breakdown of guanosine 3', 5'-cyclic monophosphate (cGMP). To date, seven members of the family have been described (PDE I-VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of tri-substituted phenyl derivatives, members of which compared to known structurally similar compounds are potent inhibitors of PDE IV at concentrations at which they have little or no inhibitory action on other PDE isoenzymes. These compounds inhibit the human recombinant PDE IV enzyme and also elevate cAMP in isolated leukocytes. The compounds of the invention are therefore of use in medicine, especially in the prophylaxis and treatment of asthma.

Thus according to one aspect of the invention, we provide a compound of formula (1)

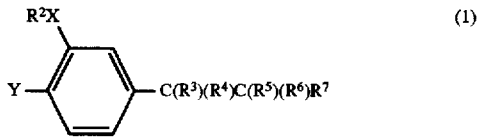

(1)

wherein

Y is a halogen atom or a group —$OR^1$ where $R^1$ is an optionally substituted alkyl group;

X is —O—, —S— or —$N(R^8)$—, where $R^8$ is a hydrogen atom or an alkyl group;

$R^2$ is an optionally substituted alkyl, alkenyl, cycloalkyl or cycloalkenyl group;

$R^3$ is a hydrogen or halogen atom or an —$OR^9$ group, where $R^9$ is a hydrogen atom or an optionally substituted alkyl, alkenyl, alkoxyalkyl, or alkanoyl group, or a formyl, carboxamido or thiocarboxamido group;

$R^4$ is a group —$(CH_2)_n Ar$, where Ar is a monocyclic or bicyclic aryl group optionally containing one or more heteroatoms selected from oxygen, sulphur or nitrogen atoms and n is zero or an integer 1,2 or 3;

$R^5$ is a $C_{3-9}$ carbocyclic ketone optionally containing one or more heteroatoms selected from oxygen, sulphur or nitrogen atoms;

$R^6$ is a hydrogen atom or an optionally substituted alkyl group;

$R^7$ is a hydrogen atom or an optionally substituted alkyl group; and the salts, solvates, hydrates and N-oxides thereof.

It will be appreciated that the compounds of formula (1) may have one or more chiral centres, depending on the nature of the groups $R^3$, $R^4$, $R^5$, $R^6$ and $R^7$. Where one or more chiral centres is present, enantiomers or diastereomers may exist, and the invention is to be understood to extend to all such enantiomers, diastereomers and mixtures thereof, including racemates.

In the compounds of formula (1), when Y is a halogen atom it may be for example a fluorine, chlorine, bromine or iodine atom.

When Y in the compounds of formula (1) is a group —$OR^1$, $R^1$ may be, for example, an optionally substituted straight or branched alkyl group, for example, an optionally substituted $C_{1-6}$ alkyl group, such as a methyl, ethyl, n-propyl or i-propyl group. Optional substitutents which may be present on $R^1$ groups include one or more halogen atoms, e.g. fluorine, or chlorine atoms. Particular substituted alkyl groups include for example —$CH_2F$, —$CH_2Cl$, —$CHF_2$, —$CHCl_2$, —$CF_3$ or -$CCl_3$ groups.

Alkyl groups represented by $R^2$, $R^6$ or $R^7$ in the compounds of formula (1) include optionally substituted straight or branched $C_{1-6}$ alkyl groups, e.g. $C_{1-3}$ alkyl groups such as methyl or ethyl groups. Optional substitutents on these groups include one, two or three substitutents selected from halogen atoms, e.g. fluorine, chlorine, bromine or iodine atoms, or hydroxyl or $C_{1-6}$ alkoxy e.g. $C_{1-3}$ alkoxy such as methoxy or ethoxy groups.

Alkenyl groups represented by $R^2$ in the compounds of formula (1) include optionally substituted straight or branched $C_{2-6}$ alkenyl groups such as ethenyl, propen-1-yl and 2-methylpropen-1-yl. Optional substitutents include those described above in relation to the groups $R^2$, $R^6$ and $R^7$.

When $R^2$ in the compounds of formula (1) is an optionally substituted cycloalkyl or cycloalkenyl group it may be for example a $C_{3-8}$ cycloalkyl group such as a cyclobutyl, cyclopentyl or cyclohexyl group or a $C_{3-8}$ cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substitutents selected from halogen atoms, e.g. fluorine, chlorine, bromine or iodine atoms, straight or branched $C_{1-6}$ alkyl e.g. $C_{1-3}$ alkyl such as methyl or ethyl, hydroxyl or $C_{1-6}$ alkoxy e.g. $C_{1-3}$ alkoxy such as methoxy or ethoxy groups.

Alkyl groups represented by $R^8$ in compounds of formula (1) include straight or branched $C_{1-6}$ alkyl groups, e.g. $C_{1-3}$ alkyl groups such as methyl or ethyl groups. Thus, for example, when X in the compounds of formula (1) is —N($R^8$)— it may be a —N($CH_3$)— or —N($CH_2CH_3$)— group. Alternatively X may be a —NH—group.

When the group $R^3$ in compounds of formula (1) is a halogen atom it may be for example a fluorine, chlorine, bromine or iodine atom.

When the group $R^3$ in compounds of formula (1) is an —$OR^9$ group it may be for example a hydroxyl group; or a group —$OR^9$ where $R^9$ is an optionally substituted straight or branched $C_{1-6}$ alkyl group, e.g. a $C_{1-3}$ alkyl group such as a methyl or ethyl group, a $C_{2-6}$ alkenyl group such as an ethenyl or 2-propen-1-yl group, a $C_{1-3}$ alkoxy $C_{1-3}$ alkyl group such as a methoxymethyl, ethoxymethyl or ethoxyethyl group, a $C_{1-6}$ alkanoyl, e.g. $C_{1-3}$ alkanoyl such as acetyl group, or a formyl [HC(O)—] or a carboxamido (CONR$^{11}$R$^{12}$) or thiocarboxamido (CSNR$^{11}$R$^{12}$) group, where $R^{11}$ and $R^{12}$ in each instance may be the same or different and is each a hydrogen atom or an optionally substituted straight or branched $C_{1-6}$ alkyl, e.g. $C_{1-3}$ alkyl group such as a methyl or ethyl group. Optional substituents which may be present on such $R^9$ groups include those described above in relation to the alkyl groups $R^2$, $R^6$ and $R^7$.

In the compounds of formula (1) the group $R^4$ may be a group —Ar, —$CH_2$Ar, —($CH_2$)$_2$Ar or —($CH_2$)$_3$Ar.

Monocyclic or bicyclic aryl groups represented by the group Ar in compounds of formula (1) include for example $C_{6-12}$ optionally substituted aryl groups, for example optionally substituted phenyl, 1-or 2-naphthyl, indenyl or isoindenyl groups.

When the monocyclic or bicyclic aryl group Ar contains one or more heteroatoms it may be for example a $C_{1-9}$ optionally substituted heteroaryl group containing for example one, two, three or four heteroatoms selected from oxygen, sulphur or nitrogen atoms. In general, Ar heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms.

Examples of heteroaryl groups represented by Ar include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2, 3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido [3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

The heteroaryl group represented by Ar may be attached to the remainder of the molecule of formula (1) through any ring carbon or heteroatom as appropriate. Thus, for example, when the group Ar is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group.

When in compounds of formula (1) the Ar group is a nitrogen-containing heterocycle it may be possible to form quaternary salts, for example N-alkyl quaternary salts and the invention is to be understood to extend to such salts. Thus for example when the group Ar is a pyridyl group, pyridinium salts may be formed, for example N-alkylpyridinium salts such as N-methylpyridinium.

The aryl or heteroaryl groups represented by Ar in compounds of formula (1) may each optionally be substituted by one, two, three or more substitutents [$R^{10}$]. The substituent $R^{10}$ may be selected from an atom or group $R^{13}$ or —Alk$^1$ ($R^{13}$)$_m$ wherein $R^{13}$ is a halogen atom, or an amino (—$NH_2$), substituted amino, nitro, cyano, hydroxyl (—OH), substituted hydroxyl, cycloalkoxy, formyl [HC(O)—], carboxyl (—$CO_2H$), esterified carboxyl, thiol (—SH), substituted thiol, —C(O)Alk$^1$, —$SO_3H$, —$SO_2$Alk$^1$, —$SO_2NH_2$, —$SO_2$NHAlk$^1$, —$SO_2$N[Alk$^1$]$_2$, —$CONH_2$, —CONHAlk$^1$, —CON[Alk$^1$]$_2$, —$NHSO_2H$, —$NHSO_2$Alk$^1$, —N[$SO_2$Alk$^1$]$_2$, —$NHSO_2NH_2$, —$NHSO_2$NHAlk$^1$, —$NHSO_2$N[Alk$^1$]$_2$, —NHC(O)Alk$^1$, or —NHC(O)OAlk$^1$ group; Alk$^1$ is a straight or branched $C_{1-6}$ alkylene, $C_{2-6}$ alkenylene, or $C_{2-6}$ alkynylene chain optionally interrupted by one, two, or three —O—, or —S— atoms or —S(O)p—, [where p is an integer 1 or 2] or —N($R^8$)— groups; and m is zero or an integer 1, 2 or 3.

When in the group —Alk$^1$($R^{13}$)$_m$ m is an integer 1, 2 or 3, it is to be understood that the substituent or substitutents $R^{13}$ may be present on any suitable carbon atom in —Alk$^1$. Where more than one $R^{13}$ substituent is present these may be the same or different and may be present on the same or different carbon atom in Alk$^1$. Clearly, when m is zero and no substituent $R^{13}$ is present or when Alk$^1$ forms part of a group such as —$SO_2$Alk$^1$ the alkylene, alkenylene or alkynylene chain represented by Alk$^1$ becomes an alkyl, alkenyl or alkynyl group.

When $R^{13}$ is a substituted amino group it may be a group —NH[Alk$^1$($R^{13a}$)$_m$] [where Alk$^1$ and m are as defined above and $R^{13a}$ is as defined above for $R^{13}$ but is not a substituted amino, a substituted hydroxyl or a substituted thiol group] or a group —N[Alk$^1$($R^{13a}$)$_m$]$_2$ wherein each —Alk$^1$($R^{13a}$)$_m$ group is the same or different.

When $R^{13}$ is a halogen atom it may be for example a fluorine, chlorine, bromine, or iodine atom.

When $R^{13}$ is a cycloalkoxy group it may be for example a $C_{5-7}$ cycloalkoxy group such as a cyclopentyloxy or cyclohexyloxy group.

When $R^{13}$ is a substituted hydroxyl or substituted thiol group it may be a group —OAlk$^1$($R^{13a}$)$_m$ or —SAlk$^1$($R^{13a}$)$_m$ respectively, where Alk$^1$, $R^{13a}$ and m are as just defined.

Esterified carboxyl groups represented by the group $R^{13}$ include groups of formula —$CO_2$Alk$^2$ wherein Alk$^2$ is a straight or branched, optionally substituted $C_{1-8}$alkyl group such as a methyl, ethyl, n-propyl, i-propyl, n-butyl, i-butyl, s-butyl or t-butyl group; a $C_{6-12}$ aryl $C_{1-8}$ alkyl group such as an optionally substituted benzyl, phenylethyl, phenylpropyl, 1 -naphthylmethyl or 2-naphthylmethyl group; a $C_{6-12}$ aryl group such as an optionally substituted phenyl, 1-naphthyl or 2-naphthyl group; a $C_{6-12}$ aryloxy $C_{1-8}$ alkyl group such as an optionally substituted phenyloxymethyl, phenyloxyethyl, 1-naphthyloxymethyl, or 2-naphthyloxymethyl group; an optionally substituted $C_{1-8}$ alkanoyloxy $C_{1-8}$ alkyl group, such as a pivaloyloxymethyl, propionyloxyethyl or propionyloxypropyl group; or a $C_{6-12}$ aroyloxy $C_{1-8}$ alkyl group such as an optionally substituted benzoyloxyethyl or benzoyloxypropyl group. Optional substituents present on the Alk$^2$ group include $R^{10}$ substituents described above.

When Alk$^1$ is present in or as a substituent $R^{10}$ it may be for example a methylene, ethylene, n-propylene, i-propylene, n-butylene, i-butylene, s-butylene, t-butylene, ethenylene, 2-propenylene, 2-butenylene, 3-butenylene, ethenylene, 2-propenylene, 2-butynylene or 3-butynylene chain, optionally interrunpred by one, two, or three —O— or —S—, atoms or —S(O)—, —S(O)$_2$— or —N($R^8$)— groups.

Particularly useful atoms or groups represented by $R^{10}$ include fluorine, chlorine, bromine or iodine atoms, or $C_{1-6}$ alkyl, e.g. methyl or ethyl, $C_{1-6}$ alkylamino, e.g. methylamino or ethylamino, $C_{1-6}$ hydroxyalkyl, e.g. hydroxymethyl or hydroxyethyl, $C_{1-6}$ alkylthiol e.g. methylthiol or ethylthiol, $C_{1-6}$ alkoxy, e.g. methoxy or ethoxy, $C_{5-7}$ cycloalkoxy, e.g. cyclo-pentyloxy, halo $C_{1-6}$ alkyl, e.g. trifluoromethyl, $C_{1-6}$ alkylamino, e.g. methylamino or ethylamino, amino (—$NH_2$), amino $C_{1-6}$ alkyl, e.g. aminomethyl or aminoethyl, $C_{1-6}$ dialkylamino, e.g. dimethylamino or diethylamino, nitro, cyano, hydroxyl (—OH), formyl [HC(O)—], carboxyl (—$CO_2H$), —$CO_2Alk^2$ [where $Alk^2$ is as defined above], $C_{1-6}$ alkanoyl e.g. acetyl, thiol (—SH), thio $C_{1-6}$ alkyl, e.g. thiomethyl or thioethyl, sulphonyl (—$SO_3H$), $C_{1-6}$ alkylsulphonyl, e.g. methylsulphonyl, aminosulphonyl (—$SO_2NH_2$), $C_{1-6}$ alkylaminosulphonyl, e.g. methylaminosulphonyl or ethylaminosulphonyl, $C_{1-6}$ dialkylaminosulphonyl, e.g. dimethylaminosulphonyl or diethylaminosulphonyl, carboxamido (—$CONH_2$), $C_{1-6}$ alkylaminocarbonyl, e.g. methylaminocarbonyl or ethylaminocarbonyl, $C_{1-6}$ dialkylaminocarbonyl, e.g. dimethylaminocarbonyl or diethylaminocarbonyl, sulphonylamino (—$NHSO_2H$), $C_{1-6}$ alkylsulphonylamino, e.g. methylsulphonylamino or ethylsulphonylamino, $C_{1-6}$ dialkylsulphonylamino, e.g. dimethylsulphonylamino or diethylsulphonylamino, aminosulphonylamino (—$NHSO_2NH_2$), $C_{1-6}$ alkylaminosulphonylamino, e.g. methylaminosulphonylamino or ethylaminosulphonylamino, $C_{1-6}$ dialkylaminosulphonylamino, e.g. dimethylaminosulphonylamino or diethylaminosulphonylamino, $C_{1-6}$ alkanoylamino, e.g. acetylamino, $C_{1-6}$ alkanoylamino $C_{1-6}$ alkyl, e.g. acetylaminomethyl or $C_{1-6}$ alkoxycarbonylamino, e.g. methoxycarbonylamino, ethoxycarbonyl-amino or t-butoxycarbonylamino groups.

Where desired, two $R^{10}$ substituents may be linked together to form a cyclic group such as a cyclic ether, e.g. a $C_{2-6}$ alkylenedioxy group such as ethylenedioxy.

It will be appreciated that where two or more $R^{10}$ substituents are present, these need not necessarily be the same atoms and/or groups. The $R^{10}$ substituents may be present at any ring carbon atom away from that attached to the rest of the molecule of formula (1). Thus, for example, in phenyl groups represented by Ar any substituent may be present at the 2-, 3-, 4-, 5- or 6- positions relative to the ring carbon atom attached to the remainder of the molecule.

In the compounds of formula (1), when an ester group is present, for example a group —$CO_2Alk^2$ this may advantageously be a metabolically labile ester.

The C3-9 carbocyclic ketone group represented by $R^5$ includes $C_{3-9}$ cyclo-aliphatic, e.g. $C_{3-9}$ cycloalkyl or $C_{3-9}$ cycloalkenyl, ketones optionally containing one or more heteroatoms selected from oxygen, sulphur or nitrogen atoms. When a heteroatom is present, the carbocyclic group may in particular be a $C_{3-5}$ heterocyclic ketone.

Particular examples of $R^5$ groups include pyrrolidone, e.g. 2-pyrrolidone, thiazolidone, e.g. 4-thiazolidone, piperidone, e.g. 4-piperidone, pyridone, e.g. 2-, 3- or 4-pyridone, quinolone, e.g. 2- or 4-quinolone, isoquinolone, e.g. 1-isoquinolone, oxazolone, e.g. 4-oxazolone, pyrazolone, e.g. 5-pyrazolone, thiazolone, e.g. 4-thiazolone and isoxazolone e.g. 5-isoxazolone groups.

The $R^5$ carbocyclic ketone groups may be substituted, for example by one or more substituents $R^{10}$ as described hereinabove. The substituent $R^{10}$ may be present at any carbon or nitrogen atom away from that attached to the rest of the molecule of formula (1). For example, when $R^5$ is a pyrazolone, the $R^{10}$ substituent may be present on a carbon or nitrogen atom at the 1-, 2- or 3-position relative to the ring carbon attached to the remainder of the molecule.

The group $R^5$ may be attached to the remainder of the molecule of formula (1) through any ring carbon or heteroatom as appropriate.

The presence of certain substitutents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds of formula (1), the group Y is preferably an —$OR^1$ group, especially where $R^1$ is an optionally substituted ethyl group or, especially, an optionally substituted methyl group. Especially useful substitutents which may be present on $R^1$ groups include one, two or three fluorine or chlorine atoms.

The group X in compounds of formula (1) is preferably —O—.

A particularly useful group of compounds of formula (1) has the formula (2):

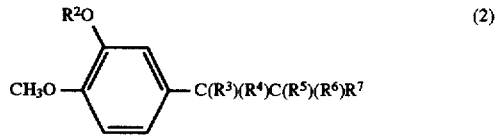

(2)

where $R^2$ is an optionally substituted cycloalkyl group; $R^3$, $R^4$, $R^5$, $R^6$ and $R^7$ are as defined for formula (1); and the salts, solvates, hydrates and N-oxides thereof.

In the compounds of formulae (1) or (2) $R^2$ is preferably an optionally substituted methyl or cyclopentyl group. In particular, $R^2$ is a cyclopentyl group.

The group $R^3$ in compounds of formulae (1) or (2) is preferably a hydrogen atom.

In compounds of formulae (1) or (2) the group $R^6$ is preferably a methyl group, or especially a hydrogen atom.

The group $R^7$ in compounds of formulae (1) or (2) is preferably a methyl group, or especially a hydrogen atom.

In one preference, $R^6$ and $R^7$ in compounds of formula (1) is each a methyl group. In another preference, one of $R^6$ or $R^7$ is a methyl group and the other is a hydrogen atom. In general, however, $R^6$ and $R^7$ is each especially a hydrogen atom.

The group $R^4$ in compounds of formulae (1) or (2) is preferably a —$CH_2Ar$ group, or, especially, an —Ar group.

Particularly useful $R^4$ groups in the compounds of formulae (1) or (2) include those $R^4$ groups in which Ar is a monocyclic aryl group optionally containing one or more heteroatoms selected from oxygen, sulphur, or, in particular, nitrogen atoms, and optionally substituted by one, two, three or more $R^{10}$ substitutents. In these compounds, when the group represented by Ar is a heteroaryl group it is preferably a nitrogen-containing monocyclic heteroaryl group, especially a six-membered nitrogen-containing heteroaryl group. Thus, in one preferred example, the group $R^4$ may be a six-membered nitrogen-containing heteroaryl group. In another preferred example $R^4$ may be a monocyclic aryl group or monocyclic heteroaryl group containing an oxygen or sulphur atom. In these examples, the six-membered nitrogen-containing heteroaryl group may be an optionally substituted pyridyl, pyridazinyl, pyrimidinyl or pyrazinyl group. Particular examples include optionally substituted 2-pyridyl, 3-pyridyl or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be a phenyl group or a substituted phenyl group, and the monocyclic heteroaryl group containing an oxygen or sulphur atom may be an optionally substituted 2-furyl, 3-furyl, 2-thienyl or 3-thienyl group.

One particularly useful group of compounds of formulae (1) or (2) is that wherein $R^4$ is a pyridyl or, especially, a monosubstituted pyridyl, or preferably a disubstituted pyridyl group, or $R^4$ is a phenyl, thienyl, furyl, or substituted phenyl, thienyl or furyl group.

In this particular group of compounds and also in general in compounds of formulae (1) or (2), when $R^4$ is a substituted phenyl group it may be for example a mono-, di- or trisubstituted phenyl group in which the substituent is an atom or group $R^{10}$ as defined above. When the $R^4$ group is a monosubstituted phenyl group the substituent may be in the 2-, or preferably 3-, or especially 4-position relative to the ring carbon atom attached to the remainder of the molecule.

When in compounds of formulae (1) or (2) $R^4$ is a substituted pyridyl group it may be for example a mono-or disubstituted pyridyl group, such as a mono- or disubstituted 2-pyridyl, 3-pyridyl or especially 4-pyridyl group substituted by one or two atoms or groups $R^{10}$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

The group $R^5$ in compounds of formulae (1) or (2) is preferably a $C_{3-5}$heterocyclic ketone, particularly an isoxazolone, pyrazolone or, especially, a pyridone group. Particularly useful groups of this type are 5-isoxalone, 5-pyrazolone or, especially, 2-pyridone groups.

A particularly useful group of compounds according to the invention has the formula (2) wherein $R^3$, $R^6$ and $R^7$ is each a hydrogen atom and $R^2$, $R^4$ and $R^5$ are as defined for formula (1); and the salts, solvates, hydrates and N-oxides thereof. Compounds of this type in which $R^2$ is a cycloalkyl or substituted cycloalkyl group, especially a substituted cyclopentyl or in particular a cyclopentyl group are particularly useful. In this group of compounds, $R^4$ is preferably a monocyclic aryl group, particularly a phenyl or substituted phenyl group or $R^4$ is a six-membered nitrogen-containing monocyclic heteroaryl group, particularly a pyridyl or substituted pyridyl group. $R^5$ is preferably a $C_{3-5}$heterocyclic ketone, particularly an isoxalone, particularly a 5-isoxazolonyl, a pyrazolone, particularly a 5-pyrazolonyl or, especially, a pyridone, particularly a 2-pyridone, group.

Particularly useful compounds according to the invention are:

(±)-3-[2-(3-Cyclopentyloxy-4-methoxyphenyl)-2-phenylethyl]-4,5-dihydro-5-isoxazolone;

(±)-3-[2-(3-Cyclopentyloxy-4-methoxyphenyl)-2-phenylethyl]-1-methyl-4,5-dihydro-5-pyrazolone;

(±)-3-[2-(3-Cyclopentyloxy-4-methoxyphenyl)-2-phenylethyl]-4,5-dihydro-5-pyrazolone;

(±)-4-[2-(3-Cyclopentyloxy-4-methoxyphenyl)-2-phenylethyl]-2-pyridone; or the resolved enantiomers thereof; and the salts, solvates, hydrates and N-oxides thereof.

The above specifically mentioned compounds exist in two enantiomeric forms. Each enantiomer is useful, as are mixtures of both enantiomers.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restonosis and ortherosclerosis.

Compounds of the invention also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention have also been found to reduce gastric acid secretion and therefore can be used to treat conditions associated with hypersecretion.

Compounds of the invention suppress cytokine synthesis by inflammatory cells in response to immune or infectious stimulation. They are, therefore, useful in the treatment of bacterial fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteo-arthritis.

Over-production of cytokines such as TNF in bacterial, fungal or viral infections or in diseases such as cancer, leads to chachexia and muscle wasting. Compounds of the invention ameliorate these symptoms with a consequent enhancement of quality of life.

Compounds of the invention elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds according to the invention may be prepared by the following processes. The symbols Y, $R^2$, $R^3$, $R^4$, $R^5$, $R^6$, $R^7$ and X, when used in the formulae below are to be understood to represent those groups described above in relation to formula (1) unless otherwise indicated. In the reactions described below it may be necessary to protect reactive functional groups, for example hydroxy, amino, thio, or carboxy groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981.] It may be that deprotection will form the last step in the synthesis of compounds of formula (1).

Thus according to a further aspect of the invention a compound of formula (1) wherein $R^3$ is a hydrogen atom or a hydroxyl group and $R^6$ and $R^7$ is each a hydrogen atom may be generally prepared by cyclisation of a compound of formula (3):

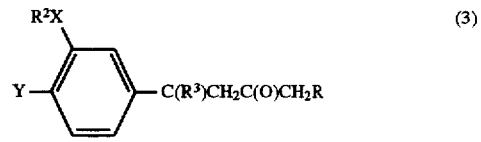

[where $R^3$ is as just defined and R is a carboxylic acid [—$CO_2H$] group or a reactive derivative thereof, or a nitrile [—CN] or an imine salt] with a bifunctional reagent $W^1R^{5a}W^2$ and, where necessary, a compound $R^{5b}W^3$ [where $W^1$, $W^2$ and $W^3$, which may be the same or different, is each a reactive functional group or a protected derivative thereof; and $R^{5a}$ and $R^{5b}$ are components of the group $R^5$ such that when added together with $W^1$, $W^2$ and $W^3$ to the group R in compounds of formula (3) the resulting group -$RW^1R^{5a}W^2$ or —$RW^1R^{5a}W^2R^{5b}W^3$ constitutes the group $R^5$].

The reaction is particularly suitable for preparing compounds of formula (1) where $R^3$ is a hydrogen atom and $R^5$ is a heterocyclic ketone, from the corresponding compound of formula (3) where $R^3$ is a hydrogen atom.

Reactive derivatives of carboxylic acids for use in this reaction include acid halides, (e.g. acid chlorides), amides, including thioamides, or esters, including thioesters. Imine salts include for example salts of formula —C(OAlk)=$NH_2^+A^-$ [where Alk is a $C_{1-4}$ alkyl group and $A^-$ is a counterion e.g. a chloride ion].

In this general reaction the reactive functional groups represented by $W^1$, $W^2$ or $W^3$ may be any suitable carbon, nitrogen, sulphur or oxygen nucleophiles. Particular examples include simple nucleophiles such as carbanions [e.g. generated by the coupling of an alkyl group with an organometallic compound], amino, thiol and hydroxyl groups.

In general, the cyclisation reaction will initially be performed in a solvent, for example an alcohol, e.g. ethanol at an elevated temperature, e.g. around the reflux temperature, where necessary in the presence of a base or a thiation reagent, e.g. Lawesson's reagent.

Active derivatives of the acids of formula (3) and other compounds of formula (3) where R is a nitrile or an imine salt may be prepared from the corresponding acids [where R is —$CO_2H$] using conventional procedures for converting carboxylic acids to such compounds, for example as described in the Examples hereinafter.

Acids of formula (3) where $R^3$ is a hydrogen atom and R is —$CO_2H$ may be prepared by hydrolysing a diester of formula (4)

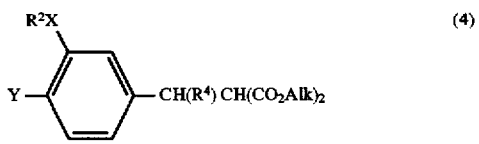

where Alk is a $C_{1-4}$ alkyl group, e.g. an ethyl group, with a base, e.g. sodium hydroxide, in a solvent, e.g. dioxane, at an elevated temperature, e.g. the reflux temperature, followed by acidification at an elevated temperature.

Diesters of formula (4) may be prepared by reacting a diester of formula (5)

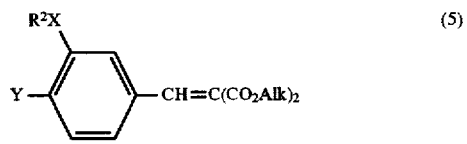

with an organometallic reagent.

Suitable organometallic reagents include Grignard reagents e.g. $R^4MgBr$, or organolithium reagents, e.g. $R^4Li$. The Grignard and lithium reagents are either known compounds or may be prepared in a similar manner to that used to synthesise the known compounds.

The reaction may be performed in a solvent such as an ether, e.g. a cyclic ether such as tetrahydrofuran, at a low temperature e.g. around –70° C. to ambient temperature.

Intermediates of formula (5) may be prepared by condensing an aldehyde of formula (6)

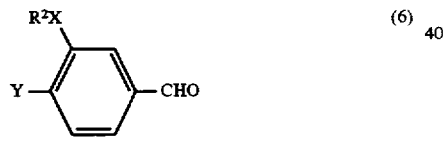

with a malonate, e.g. diethylmalonate, if necessary in the presence of catalysts, e.g. piperidine and acetic acid, in an inert solvent, e.g. toluene, at elevated temperature, e.g. the reflux temperature.

Aldehydes of formula (6) may be prepared by alkylation of a corresponding compound of formula (7)

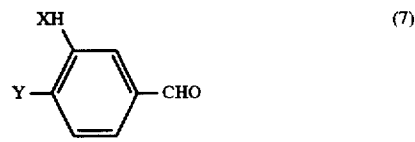

using a compound $R^2Hal$ [where Hal is a halogen atom such as a bromine atom] using the reagents and conditions described hereinafter for the alkylation of intermediates of formula (10).

Intermediates of formula (7) are either known compounds or may be prepared from known starting materials by methods analogous to those used for the preparation of the known compounds.

Intermediates of formula (3) where $R^3$ is a hydroxyl group may be prepared by reaction of a ketone of formula (8)

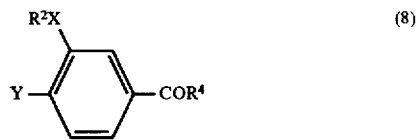

With an organometallic reagent $RCH_2COCH_2Z$, where Z is a metal atom, for example a lithium atom.

The reaction may be performed in a solvent such as an ether, e.g. a cyclic ether such as tetrahydrofuran, at a low temperature, e.g. around –70° C. to ambient.

Reagents $RCH_2COCH_2Z$ are either known compounds or may be preapred, preferably in situ during the above process, by reaction of a compound $AlkCH_2Z$ [where Alk is an alkyl group such as a n-propyl group] with a compound $RCH_2COCH_3$, where necessary in the presence of a base such as an amine e.g. diisopropylamine using the above-mentioned conditions.

Ketones of formula (8) may be prepared by oxidation of a corresponding alcohol of formula (9):

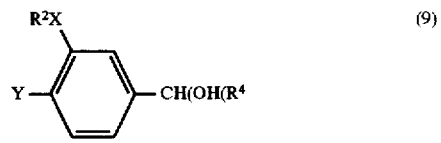

using an oxidising agent such as manganese dioxides in a solvent such as dichloromethane at ambient temperature.

Alcohols of formula (9) may be preapred by reaction of an aldehyde of formula (6) with an organometallic reagent such as a Grignard reagent $R^4MgBr$ or organolithium compound $R^4Li$ as described above for the preparation of diesters of formula (4)

In another process according to the invention, a compound of formula (1) may be prepared by alkylation of a compound of formula (10):

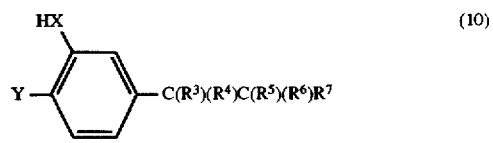

using a reagent $R^2L$, where L is a leaving group.

Leaving groups represented by L include halogen atoms such as iodine or chlorine or bromine atoms or sulphonyloxy groups such as arylsulphonyloxy groups, e.g. p-toluenesulphonyloxy.

The alkylation reaction may be carried out in the presence of a base, e.g. an inorganic base such as a carbonate, e.g. caesium or potassium carbonate, an alkoxide, e.g. potassium-t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at ambient temperature or above e.g. around 40° C. to 50° C.

Intermediates of formula (10) may be obtained from the corresponding protected compound of formula (11):

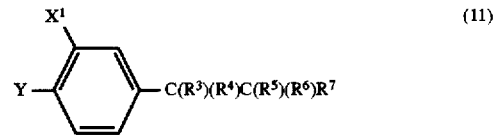

wherein $X^1$ is a protected hydroxy, thio or amino group using conventional procedures [see Green, T. W. ibid]. Thus, for example, where $X^1$ is a t-butyldimethylsilyloxy group, the required hydroxyl group may be obtained by treatment of the protected intermediate with tetrabutylammonium fluoride. The protected intermediate of formula (11) may be prepared in an analogous manner to the compounds of formula (1) using the reactions described herein and appropriately protected intermediates.

In yet another process according to the invention, a compound of formula (1) where $R^5$ is a pyrid-2-one group may be prepared by displacement of a halogen atom from the corresponding 2-halopyridine of formula (1). The reaction may be performed using a base, for example an alkali metal base such as sodium hydroxide, optionally at an elevated temperature, in a solvent such as a glycol, e.g. diethylene glycol. The halopyridine starting materials for this reaction are either known compounds (see for example European Patent Specification No. 626939) or may be prepared by methods similar to those used for the preparation of the known compounds.

Compounds of formula (1) may also be prepared by interconversion of other compounds of formula (1). Thus, for example, a group represented by $R^4$ in compounds of formula (1) may be substituted in the aryl or heteroaryl portions by any of the groups $R^{10}$ by an appropriate substitution reaction using the corresponding unsubstituted compound of formula (1) and a $R^{10}$ containing nucleophile or electrophile.

In another example of an interconversion process a compound of formula (1) wherein the aryl or heteroaryl group in $R^4$ contains a —$CH_2NH_2$ substituent may be prepared by reduction of a corresponding compound wherein $R^4$ contains a nitrile group, using for example a complex metal hydride such as lithium aluminium hydride in a solvent such as an ether e.g. diethylether.

In a further example, a compound of formula (1) wherein the aryl or heteroaryl group in $R^4$ contains an alkanoylamino or alkanoylaminoalkyl substituent may be prepared by acylation of a corresponding compound wherein $R^4$ contains a —$NH_2$ or alkylamino group by reaction with an acyl halide in the presence of a base, such as a tertiary amine e.g. triethylamine in a solvent such as dichloromethane.

In yet another example of an interconversion process, compounds of formula (1) wherein $R^4$ is substituted by an ester [$CO_2Alk^2$], e.g. an ethanoate, may be prepared by esterification of a corresponding compound wherein $R^4$ contains a carboxylic acid, using an acid halide, such as an acid chloride, e.g. acetyl chloride, in an alcohol, such as ethanol, at an elevated temperature, such as the reflux temperature.

Compounds of formula (1) wherein $R^4$ is substituted by a carboxylic acid may be prepared from the corresponding compound wherein $R^4$ contains a formyl group, by oxidation with an oxidising agent, e.g. potassium permanganate, in a solvent, such as an alcohol, e.g. tert-butanol, at ambient temperature.

In a further interconversion reaction, compounds of formula (1) wherein $R^4$ is substituted by an aminoalkyl group, such as dimethyl-aminomethyl, may be prepared by reductive amination of a corresponding compound wherein $R^4$ contains a formyl group, using an amine, e.g. dimethylamine, in the presence of a reducing agent, e.g. sodium cyanoborohydride, if necessary in the presence of a catalyst, e.g. ethanolic HCl, in a solvent, such as an alcohol, e.g. methanol, at ambient temperature.

In another example of an interconversion reaction a compound of formula (1) wherein $R^4$ is substituted by a formyl group, may be reduced to the corresponding alcohol, e.g. where $R^4$ contains a hydroxy-methyl group, using a reducing agent, e.g. sodium borohydride, in a solvent, such as an alcohol, e.g. ethanol, at a temperature from around 20° C. to ambient temperature. The resulting alcohol may then be converted to the corresponding alkoxy derivative, e.g. methoxymethyl, by reaction with an alkyl halide or alkyl sulphonate using the methods and reagents described above for the alkylation of intermediates of formula (8).

In a further example of an interconversion process compounds of formula (1) wherein $R^4$ contains a carboxamido (—$CONHR^{11}$) or an aminocarbonyl (—$NHCOR^{11}$) group may be prepared by reaction of the corresponding compound wherein $R^4$ contains a —$CO_2H$ or a —$NH_2$ group respectively by reaction with a carbamate, such as isobutyl chloroformate or ethyl chloroformate, in the presence of a base, such as an amine, e.g. triethyl-amine or N-methylmorpholine, in a solvent, such as dichloromethane, or a mixture of solventrs, e.g. tetrahydrofuran and dimethylformamide, at a temperature from around –20° C. to room temperature.

In a still further interconversion reaction, compounds of formula (1) wherein $R^4$ is substituted by a —$NHCONHR^{11}$ group may be prepared by reacting a corresponding compound wherein $R^4$ is substituted by an amino (—$NH_2$) group, with an isocyanate, e.g. ethyl isocyanate, in a solvent, e.g. dichloromethane, at ambient temperature.

In another example of an interconversion process, compounds of formula (1) wherein $R^7$ is an alkyl group, may be prepared by interconversion of a compound of formula (1) where $R^7$ is a hydrogen atom by reaction with a compound $R^7L$, where L is a leaving group, for example a halogen atom, such as chlorine, in the presence of a base, for example lithium diisopropylamide, in a solvent such as tetrahydrofuran, at low temperature, such as 0° C.

Compounds of formula (1) wherein $R^3$ is an $OR^9$ group where $R^9$ is an alkyl, alkoxyalkyl, formyl or alkanoyl group, may be prepared in another example of an interconversion process by reaction of a compound of formula (1) where $R^3$ is a —OH group with a compound $R^9L$ (where $R^9$ is as just defined and L is a leaving group as described above), in a solvent, such a dichloromethane or tetrahydrofuran in the presence of base, for example triethylamine or potassium tert-butoxide, at room temperature.

In a further interconversion process compounds of formula (1) wherein $R^9$ is a carboxamido (—$CONHR^{11}$) or a thiocarboxamido (—$CSNHR^{11}$) group, may be prepared by reaction of a compound of formula (1) wherein $R^3$ is a hydroxyl group with an isocyanate $R^{11}NCO$ or an isothiocyanate $R^{11}NCS$, in a solvent, for example chloroform, in the presence of a base, for example diisopropylethylamine, at ambient temperature. The isocyanate $R^{11}NCO$ and isothiocyanate $R^{11}NCS$ are known compounds or may be prepared in a conventional manner.

In a further example, a compound of formula (1) wherein $R^9$ is a $CONR^{11}R^{12}$ group may be prepared by reaction of a compound of formula (1) wherein $R^9$ is a $CONHR^{11}$ group with a reagent $R^{12}L$ (where L is a leaving group as described above) in the presence of a base, for example sodium hydride, in a solvent, such as tetrahydrofuran, at low temperature, for example 0° C.

In another example, an isothiocyanate of formula (1) where $R^9$ is —$CSNR^{11}R^{12}$ may be prepared by reacting a compound of formula (1) wherein $R^9$ is a (—$CONR^{11}R^{12}$) group with a thiation reagent, such as Lawesson's Reagent, in an anhydrous solvent, for example toluene, at elevated temperature, such as the reflux temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid or base in a suitable solvent e.g. an organic solvent such as an ether, using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral acid or base. Suitable chiral acids include, for example, tartaric acid and other tartrates such as dibenzoyl tartrates and ditoluoyl tartrates, sulphonates such as camphor sulphonates, mandelic acid and other mandelates and phosphates such as 1,1'-binaphthalene-2,2'-diyl hydrogen phosphate. The diastereomers may then be separated by any convenient means, for example by crystallisation and the desired enantiomer recovered, e.g. by treatment with an acid or base in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

The following examples illustrate the invention. The following abbreviations are used: DMF—dimethylformamide; THF—tetrahydrofuran; DME—dimethoxyethane; EtOAc—ethyl acetate; Et$_2$O—diethylether; Et$_3$N—triethylamine; BuLi—butyllithium; LDA—lithium diisopropylamide; EtOH—ethanol; RT—room temperature.

All $^1$Hnmr spectra were obtained at 300 MHz unless specified otherwise.

INTERMEDIATE 1

3-Cyclopentyloxy-4-methoxybenzaldehyde

Cs$_2$CO$_3$ (214 g, 0.66 mol) was added to a mixture of 3-hydroxy-4-methoxybenzaldehyde (100 g, 0.66 mol) and cyclopentyl bromide (98 g, 0.66 mol) in anhydrous DMF (500 ml). The reaction mixture was stirred at RT for 16 h then treated with a further portion of cyclopentyl bromide (98 g, 0.66 mol) and Cs$_2$CO$_3$ (214 g, 0.66 mol). After a further 6 h at RT, the mixture was filtered and concentrated in vacuo. The residue was dissolved in CH$_2$Cl$_2$ (300 ml) and washed with NaOH solution (10%; 2×150 ml). The organic layer was dried (MgSO$_4$), concentrated in vacuo, and distilled (150° C., 10$^{-2}$ mbar) to afford the title compound (130 g) as a viscous colourless oil. $\delta_H$ (CDCl$_3$) 1.5–2.0 (8H, br m, CH$_2$)$_4$), 3.87 (3H, s, OMe), 4.80 (1H, br m, OCHCH$_2$), 6.90 (1H, d, J 8.7 Hz, ArH ortho to OMe), 7.30–7.45 (2H, m, 2×ArH meta to OMe), and 9.77 (1H, s, ArCHO).

INTERMEDIATE 2

Ethyl 3-(3—Cyclopentyloxy-4-methoxyphenyl)-2-ethoxycarbonyl propenoate

A mixture of Intermediate 1 (109.8, 499.1 mmol), diethyl malonate (79.96, 499.1 mmol), piperidine (2.5 ml) and CH$_3$CO$_2$H (12 ml) in toluene (700 ml) was heated to reflux in a Dean-Stark apparatus for 20 h. Further portions of diethyl malonate (9.6 g, 59.9 mmol), piperidine (2.5 ml), and CH$_3$CO$_2$H (12 ml) were added and heating continued as before for 15 h. The reaction mixture was concentrated in vacuo to afford the title compound (217 g) as a brown oil. $\delta_H$ (CDCl$_3$) 1.33 (6H, t, J 7.1 Hz, 2×CO$_2$CH$_2$Me), 1.5–2.05 (8H, br m, (CH$_2$)$_4$), 3.88(3H, s, OMe), 4.30 (2H, q, J 7.1 Hz, CO$_2$CH$_2$Me), 4.36 (2H, q, J 7.1 Hz, CO$_2$CH$_2$Me), 4.73 (1H, br m, OCH), 6.85 (1H, d, J 8.1 Hz, ArH ortho to OMe), 7.0–7.1 (2H, m, 2×ArH meta to OMe), and 7.63 (1H, s, HC=CCO$_2$Et).

INTERMEDIATE 3

Diethyl 2-r(3—Cyclopentyloxy-4-methoxyphenyl) phenylmethylpropan-1-3-dioate Phenylmagnesium bromide (1.0M in THF; 340 ml, 340 mmol, 1.29 eq) was added over 1.5 h to a solution of Intermediate 2 (95.6 g, 264 mmol) in THF (200 ml) at −60° C. and stirred at this temperature for a further 5 h. The reaction mixture was allowed to warm to −20° C., quenched with 10% aqueous NH$_4$Cl (200 ml), then extracted with EtOAc (3×100 ml). The extract was dried (MgSO$_4$), concentrated in vacuo, the residual brown oil dissolved in EtOH and allowed to crystallise overnight to afford the title compound (74.9 g) as a white solid. m.p. 97°–98° C. $\delta_H$ (CDCl$_3$) 1.01 (6H, t, J 7.1 Hz, CO$_2$CH$_2$Me), 1.05 (3H, t, J 7.1 Hz, CO$_2$CH$_2$Me), 1.5–2.0 (8H, br m, (CH$_2$)$_4$), 3.77 (3H, s, OMe), 3.9–4.1 (4H, m, 2×CO$_2$CH$_2$Me), 4.26 (1H, d, J 12.1 Hz, CHCHCO$_2$Et), 4.67 (1 H, d, J 12.1 Hz, C HCHCO$_2$Et), 4.71 (1H, br m, OCH), 6.7–6.85 (3H, m, C$_6$H$_3$), and 7.15–7.35 (5H, m, C$_6$H$_5$).

INTERMEDIATE 4

3-(3-Cyclopentyloxy-4-methoxyphenyl)-3-phenylpropanoic acid

A mechanically stirred solution of Intermediate 3 (70.3 g, 0.160 mol) in NaOH solution (8M; 600 ml) and dioxane (600 ml) was heated to reflux for 7 h. The reaction mixture was cooled, concentrated hydrochloric acid (about 400 ml) added dropwise to pH4 and heating carried overnight to give a homogenous solution. The dioxane was removed in vacuo and the mixture partitioned between CH$_2$Cl$_2$ (500 ml) and H$_2$O (500 ml). The organic layer was separated and combined with further CH$_2$Cl$_2$ extracts (3×150 ml). The extract was dried (MgSO$_4$) and concentrated in vacuo to give the title compound (55 g) as a yellow solid. $\delta_H$ (CDCl$_3$) 1.5–2.0 (8H, br m, (CH$_2$)$_4$), 3.04 (2H, d, J 7.9 Hz, CHC H$_2$CO$_2$H), 3.80 (3H, s, OMe), 4.45 (1H, t, J 7.9 Hz C HCH$_2$CO$_2$H), 4.70 (1H, br m, OCH), 6.7–6.8 (3H, m, C$_6$ H$_3$), and 7.15–7.35 (5H, m, C$_6$H$_5$) (N.B. CO$_2$H not observed).

INTERMEDIATE 5

3-(3-Cyclopentyloxy-4-methoxyphenyl)-3-phenylpropanoyl chloride

SOCl$_2$ (14.8 ml, 24.1 g, 3 eq) was added to a solution of Intermediate 4 (23.0 g, 67.5 mmol) in CH$_2$Cl$_2$ (250 ml) and then heated to reflux for 6 h. The reaction mixture was allowed to stir at RT overnight then concentrated in vacuo to afford the title compound (23.7 g) as a dark brown oil. $\delta_H$ (CDCl$_3$) 1.5–2.0 (8H, br m, (CH$_2$)$_4$), 3.62 (2H, d, J 8.0 Hz, CHCH$_2$COCl), 3.82 (3H, s, OMe), 4.56 (1H, t, J 8.0 Hz, C HCH₂COCl), 4.73 (1H, br m, OC$\underline{H}$), 6.7–6.85 (3H, m, C₆$\underline{H}$₃), and 7.15–7.4 (5H, m, C₆$\underline{H}$₅).

INTERMEDIATE 6

Ethyl 5-(3-Cyclopentyloxy-4-methoxyphenyl)-3-oxo-5-phenyl-pentanoate n-BuLi (1.6$\underline{M}$ in hexanes; 29.3 ml, 46.9 mmol, 4.2 eq) was added dropwise at −50° C. to a solution of potassium ethyl malonate (2.95 g, 22.3 mmol, 2.1 eq) in THF (60 ml). The reaction mixture was allowed to warm to −10° C., stirred for 10 min, then recooled to −65° C. and treated dropwise with a precooled solution of Intermediate 5 (4.0 g, 11.1 mmol) in THF (20 ml). The reaction mixture was stirred at −65° C. for 20 min, then poured into a stirred mixture of Et₂O (100 ml) and aqueous HCl (1$\underline{M}$; 150ml). After 0.5 h, the organic phase was separated and combined with further Et₂O extracts (2×75 ml). The extract was dried (MgSO₄), concentrated in vacuo, and the residual oil subjected to chromatography (SiO₂; 40% Et₂O-hexane) to afford a colourless oil (3.4 g) which crystallised on standing to give the title compound as a white solid. m.p. 56°–58° C. (EtOH). $\delta_H$ (CDCl₃) 1.24 (3H, t, $\underline{J}$ 7 Hz, CO₂CH₂$\underline{Me}$), 1.5–1.9 (8H, br m, (C$\underline{H}$₂)₄), 3.27 (2H, d $\underline{J}$ 7.5 Hz, CHC$\underline{H}$₂CO), 3.33 (2H, s, C$\underline{H}$₂CO₂Et), 3.79 (3H, s, O$\underline{Me}$), 4.14 (2H, q, $\underline{J}$ 7 Hz, CO₂C$\underline{H}$₂Me), 4.52 (1H, t, $\underline{J}$ 7.5 Hz, C$\underline{H}$CH₂CO), 4.69 (1H, m, OC $\underline{H}$), 6.7–6.8 (3H, m, C₆$\underline{H}$₃), and 7.1–7.35 (5H, m, C₆$\underline{H}$₅).

EXAMPLE 1 a) (±)-3-[2-(3-Cyclopentyloxy-4-methoxyphenyl)-2-phenylethyl]-4,5-dihydro-5-isoxazolone A mixture of Intermediate 6 (800 mg, 1.95 mmol) and hydroxylamine hydrochloride (203 mg, 2.91 mmol) in EtOH (20 ml) was heated to reflux for 4 h then left to stand at RT overnight. The reaction mixture was concentrated in vacuo and dissolved in water (20 ml) containing Et₃N (0.5 ml). The supernatant was decanted off and the oily solid washed with water (20 ml). Chromatography (SiO₂; CH₂Cl₂ to 5% MeOH/CH₂Cl₂) afforded a pale yellow solid (500 mg) which was recrystallised from EtOH (25 ml) to afford the title compound (305 mg), as pale yellow microneedles m.p. 137–139° C. (Found: C, 73.02; H, 6.65; N, 3.55. C₂₃H₂₅NO₄ requires C, 72.80; H, 6.64; N, 3.69%); $\delta_H$ (CDCl₃) 1.5–1.95 (8H, br m, (CH₂)₄), 3.0 (2H, s, C$\underline{H}$₂CO), 3.20 (2H, d, $\underline{J}$ 8.3 Hz, C$\underline{H}$₂CHPh), 3.81 (3H, s, O$\underline{Me}$), 4.18 (1H, t, $\underline{J}$ 8.3 Hz, CH₂C$\underline{H}$Ph), 4.71 (1H, br m, OC$\underline{H}$), 6.7–6.85 (3H, m, C₆$\underline{H}$₃), and 7.2–7.35 (5H, m, C₆$\underline{H}$₅).

The following compound was prepared in a manner similar to the compound of Example 1a.

b) (±)-3-[2-(3-Cyclopentyloxy4-methoxyphenyl)-2-phenylethyl]-1-methyl-4,5-dihydro-5-pyrazolone From Intermediate 6 (750 mg, 1.83 mmol) and methylhydrazine (101 mg, 120 μL, 2.2 mmol) in EtOH (20 ml). Trituration with a mixture of Et₂O (20 ml), EtOAc (3 ml), and hexane (5 ml) gave a solid which was filtered off, washed with cold Et₂O (5 ml) and dried in vacuo to afford the title compound (485 mg) as a white solid m.p. 105°–108° C. (Found: C, 73.56; H, 7.06; N, 6.98. C₂₄H₂₈N₂O₃ requires C, 73.44; H, 7.19); N, 7.14%); $\delta_H$ (CDCl₃) 1.5–1.9 (8H, br m, (CH₂)₄), 2.87 (2H, s, C$\underline{H}$₂CO), 3.13 (2H, d, $\underline{J}$ 8.2 Hz, C$\underline{H}$₂CHPh), 3.23 (3H, s, N$\underline{Me}$), 3.81 (3H, s, O$\underline{Me}$), 4.18 (1H, t, $\underline{J}$ 8.2 Hz, CH₂C$\underline{H}$Ph), 4.7 (1H, br m, OC$\underline{H}$), 6.7–6.8 (3H, m, C₆$\underline{H}$₃), and 7.15–7.35 (5H, m, C₆$\underline{H}$₅).

EXAMPLE 2

(±)-4-[2-(3-Cyclopentyloxy-4-methoxyphenyl)-2-phenylethy]-1-2-pyridone

A solution of (+)-2-chloro-4-[2-(3-cyclopentyloxy-4-methoxyphenyl)-2-phenylethyl]pyridine [4.69 mg, 1.15 mmol; Example 26 of European Patent Specification No. 626939] and sodium hydroxide (2 g, 50 mmol) in dietheylene glycol (10ml) was heated at 170° C. for 2 h. The reaction mixture was cooled to RT and the resultant brown gel was partitioned between Et₂O (80 ml) and water (60 ml). The organic layer was washed with saturated brine (50 ml), dried (MgSO₄) and evaporated to give a dark brown gum. Chromatography on silica, eluting with 1→4% methanol in CH₂Cl₂, afforded the title compund as a pale brown gum (40 mg). $\delta_H$ (CDCl₃) 1.55–1.90 (8H, m, C$\underline{H}$₂C), 3.17 (2H, d, $\underline{J}$ 8 Hz, C$\underline{H}$₂Py), 3.78 (3H, s, OMe), 4.14 (1H, t, $\underline{J}$ 8 Hz, C HCH₂Py), 4.67 (1H, m, CO), 5.97 (1H, d, $\underline{J}$ 7 Hz, $\underline{H}$a Py), 6.25 (1H, s, $\underline{H}$c Py), 6.68–6.77 (3H, m, Ar $\underline{H}$d-f), 7.13–7.29 (6H, m, Ph+Hb).

FORMULATION EXAMPLES

The compounds of the invention may be formulated for pharmaceutical use in a number of forms using any suitable excipients. Thus, for example, for oral use the compounds of the invention such as the compounds of the Examples may be formulated as a solid dosage form, by mixing an appropriate weight of compound (for example 50 mg) with maize starch (50–99% w/w), anhydrous colloidal silica (0–10% w/w) and organic or inorganic acid (up to 1% w/w), to fill capsules of an appropriate size, e.g. white opaque hard gelatine capsules size 3. If desired the same mixture may be compressed into tablets.

The activity and selectivity of compounds according to the invention was demonstrated in the following tests. In these tests the abbreviation FMLP represents the peptide N-formyl-met-leu-phe.

Isolated Enzyme

The potency and selectivity of the compounds of the invention was determined using distinct PDE isoenzymes as follows:

i. PDE I, rabbit heart
ii. PDE II, rabbit heart
iii. PDE III, rabbit heart, Jurkat cells
iv. PDE IV, HL60 cells, rabbit brain, rabbit kidney and human recombinant PDE IV
v. PDE V, rabbit lung, guinea pig lung A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, *TIPS*, 11, 150). These recombinant enzymes, particularly the human eosinophil recombinant PDE IV, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50 mM 2-[|tris (hydroxymethyl)methyl]amino]-1-ethane-sulphonic acid (TES) —NaOH buffer (pH 7.5), 10 mM MgCl₂, 0.1 μM [³H]-cAMP and vehicle or various concentrations of the test compounds. The reaction was initiated by addition of enzyme and conducted at 30° C. for between 5 to 30 mins.

The reaction was terminated by addition of 50 μl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES-NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction.

Compounds according to the invention such as compounds of the Examples herein cause a concentration-dependent inhibition of recombinant PDE IV at 0.1–1000 nM with little or no activity against PDE I, II, III/I or V at concentrations up to 100 μM.

2. The Elevation of CAMP in Leukocytes

The effect of compounds of the invention on intracellular cAMP was investigated using human neutrophils or guinea pig eosinophils.

Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 10 μM.

3. Suppression of Leukocyte Function

Compounds of the invention were investigated for their effects on superoxide generation, chemotaxis and adhesion of neutrophils and eosinophils. Isolated leukocytes were incubated with dihydrocytochalasin B for superoxide generation only and test compound prior to stimulation with FMLP. The most potent compounds of the Examples caused a concentration-dependent inhibition of superoxide generation, chemotaxis and adhesion at concentrations of 0.1 nM to 1 μM.

Lipopolysaccharide (LPS)-induced synthesis of tumour necrosis factor (TNF) by human peripheral blood monocytes (PBM) is inhibited by compounds of the Examples at concentrations of 0.01 nM to 10 μM.

4. Adverse Effects

In general, in our tests, compounds of the invention have had no observed toxic effects when administered to animals at pharmacologically effective doses.

We claim:

1. A compound of formula (1):

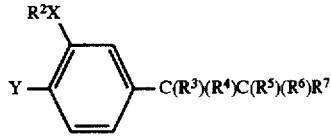

wherein:

Y is a halogen atom or a group —OR$^1$ where R$^1$ is an optionally substituted alkyl group;

X is —O—, —S— or —N(R$^8$)—, where R$^8$ is a hydrogen atom or an alkyl group;

R$^2$ is an optionally substituted alkyl, alkenyl, cycloalkyl or cycloalkenyl group;

R$^3$ is a hydrogen or halogen atom or an —OR$^9$ group, where R$^9$ is a hydrogen atom or an optionally substituted alkyl, alkenyl, alkoxyalkyl or alkanoyl group, or a formyl, carboxamido or thiocarboxamido group;

R$^4$ is a group —(CH$_2$)$_n$Ar, where Ar is a monocyclic or bicyclic aryl group optionally containing one or more heteroatoms selected from oxygen, sulfur or nitrogen atoms, and n is zero or an integer 1, 2 or 3;

R$^5$ is a C$_{3-9}$ carbocyclic ketone optionally containing one or more heteroatoms selected from oxygen, sulphur or nitrogen atoms;

R$^6$ is a hydrogen atom or an optionally substituted alkyl group;

R$^7$ is a hydrogen atom or an optionally substituted alkyl group; and the salts, solvates and hydrates thereof;

with the proviso that R$^4$ is a 6-membered nitrogen-containing heteroaryl group or R$^5$ is a 6-membered nitrogen-containing-heterorylic ketone.

2. A compound according to claim 1, wherein Y is a group —OR$^1$ and R$^1$ is an optionally substituted straight or branched C$_{1-3}$ alkyl group.

3. A compound according to claim 2, wherein R$^1$ is a —CH$_3$ group.

4. A compound according to claim 1 wherein X is —O—.

5. A compound according to claim 1 wherein R$^2$ is a cyclopentyl group.

6. A compound according to claim 1 wherein R$^3$, R$^6$ and R$^7$ is each a hydrogen atom.

7. A compound according to claim 1 wherein R$^4$ is a group —CH$_2$Ar or Ar, wherein Ar is a monocyclic aryl group optionally containing one or more heteroatoms selected from oxygen, sulphur or nitrogen atoms.

8. A compound according to claim 7, wherein R$^4$ is an optionally substituted pyridyl, phenyl, thienyl or furyl group.

9. A compound according to claim 1 where R$^5$ is a C$_{3-5}$ heterocyclic ketone.

10. A compound according to claim 9, wherein R$^5$ is an optionally substituted pyrrolidone, thiazolidone, piperidone, pyridone, quinolone, isoquinolone, oxazolone, pyrazolone, thiazolone or isoxazolone group.

11. A pharmaceutical composition comprising a compound of formula (1):

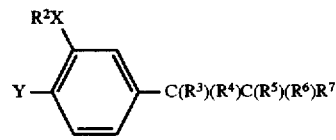

wherein:

Y is a halogen atom or a group —OR$^1$ where R$^1$ is an optionally substituted alkyl group;

X is —O—, —S— or —N(R$^8$)—, where R$^8$ is a hydrogen atom or an alkyl group;

R$^2$ is an optionally substituted alkyl, alkenyl, cycloalkyl or cycloalkenyl group;

R$^3$ is a hydrogen or halogen atom or an —OR$^9$ group, where R$^9$ is a hydrogen atom or an optionally substituted alkyl, alkenyl, alkoxyalkyl or alkanoyl group, or a formyl, carboxamido or thiocarboxamido group;

$R^4$ is a group —$(CH_2)_n Ar$, where Ar is a monocyclic or bicyclic aryl group optionally containing one or more heteroatoms selected from oxygen, sulfur or nitrogen atoms and n is zero or an integer 1 2 or 3;

$R^5$ is a $C_{3-9}$ carbocyclic ketone optionally containing one or more heteroatoms selected from oxygen, sulphur or nitrogen atoms;

$R^6$ is a hydrogen atom or an optionally substituted alkyl group;

$R^7$ is a hydrogen atom or an optionally substituted alkyl group; and the salts, solvates and hydrates thereof;

with the proviso that $R^4$ is a 6-membered nitrogen-containing heteroaryl group or $R^5$ is a 6-membered nitrogen-containing heterocylic ketone; together with one or more pharmaceutically acceptable carriers, excipients or diluents.

12. A compound according to claim 1 wherein $R^4$ is a group —$(CH_2)_n Ar$, where Ar is a monocyclic or bicyclic aryl group containing one or more nitrogen heteroatoms.

13. A compound according to claim 1 wherein $R^5$ is a $C_{3-9}$ carbocyclic ketone containing one or more nitrogen heteroatoms.

14. A compound according to claim 10 wherein $R^5$ is an optionally substituted pyrrolidone, piperidone, pyridone, quinolone or isoquinolone group.

15. A compound according to claim 14 wherein $R^5$ is an optionally substituted pyridone group.

16. A compound according to claim 15 wherein said pyridone group is unsubstituted.

17. A compound according to claim 8 wherein $R^4$ is an optionally substituted phenyl group.

18. A compound according to claim 17 wherein said phenyl group is unsubstituted.

19. A compound which is (±)-4-[2-(3-cyclopentyloxy-4-methoxyphenyl)-2-phenylethyl]-2-pyridone or a resolved enantiomer thereof; or a salt, solvate or hydrate thereof.

20. A pharmaceutical composition comprising, in combination with one or more pharmaceutically acceptable carriers, excipients or diluents, (±)-4-[2-(3-cyclopentyloxy-4-methoxyphenyl)-2-phenylethyl]-2-pyridone or a resolved enantiomer thereof; or a salt, solvate or hydrate thereof.

21. A method of preventing or treating an inflammatory disease in a patient comprising administering to said patient a selective inhibitor of a phosphodiesterase (PDE) IV isoenzyme in an amount sufficient to elevate intracellular levels of adenosine 3', 5'-cyclic monophosphate (cAMP) said inhibitor being selected from a compound of formula (1):

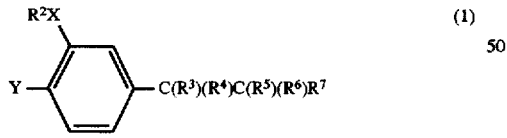

(1)

wherein

Y is a halogen atom or a group —$OR^1$ where $R^1$ is an optionally substituted alkyl group;

X is —O—, —S— or —$N(R^8)$—, where $R^8$ is a hydrogen atom or an alkyl group;

$R^2$ is an optionally substituted alkyl, alkenyl, cycloalkyl or cycloalkenyl group;

$R^3$ is a hydrogen or halogen atom or an —$OR^9$ group, where $R^9$ is a hydrogen atom or an optionally substituted alkyl, alkenyl, alkoxyalkyl or alkanoyl group, or a formyl, carboxamido or thiocarboxamido group;

$R^4$ is a group —$(CH_2)_n Ar$ where Ar is a monocyclic or bicyclic aryl group optionally containing one or more heteroatoms selected from oxygen sulfur or nitrogen atoms, and n is zero or an integer 1, 2 or 3;

$R^5$ is a $C_{3-9}$ carbocyclic ketone optionally containing one or more heteroatoms selected from oxygen, sulphur or nitrogen atoms;

$R^6$ is a hydrogen atom or an optionally substituted alkyl groups;

$R^7$ is a hydrogen atom or an optionally substituted alkyl group; and the salts, solvates and N-oxides thereof;

with the proviso that $R^4$ is a 6-membered nitrogen-containing heteroaryl group or $R^5$ is a 6-membered nitrogen-containing heterocylic ketone.

22. A method according to claim 21 wherein said inflammatory disease is asthma.

23. A method according to claim 21 wherein said inflammatory disease is selected from the group consisting of inflammatory airway disease, chronic bronchitis, inflammatory arthritis, adult respiratory distress syndrome, allergic rhinitis, and allergic conjunctivitis.

24. A process for the preparation of a compound of formula (1):

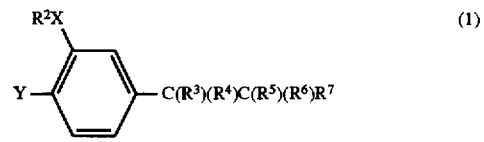

(1)

wherein:

Y is a halogen atom or a group —$OR^1$ where $R^1$ is an optionally substituted alkyl group;

X is —O—, —S— or —$N(R^8)$—, where $R^8$ is a hydrogen atom or an alkyl group;

$R^2$ is an optionally substituted alkyl, alkenyl, cycloalkyl or cycloalkenyl group;

$R^3$ is a hydrogen or halogen atom or an —$OR^9$ group, where $R^9$ is a hydrogen atom or an optionally substituted alkyl, alkenyl, alkoxyalkyl or alkanoyl group, or a formyl, carboxamido or thiocarboxamido group;

$R^4$ is a group —$(CH_2)_n Ar$, where Ar is a monocyclic or bicyclic aryl group optionally containing one or more heteroatoms selected from oxygen, sulfur or nitrogen atoms, and n is zero or an integer 1, 2 or 3;

$R^5$ is a $C_{3-9}$ carbocyclic ketone optionally containing one or more heteroatoms selected from oxygen, sulphur or nitrogen atoms;

$R^6$ is a hydrogen atom or an optionally substituted alkyl group;

$R^7$ is a hydrogen atom or an optionally substituted alkyl group; and the salts, solvates and hydrates thereof;

with the proviso that $R^4$ is a 6-membered nitrogen-containing heteroaryl group or $R^5$ is a 6-remembered nitrogen-containing heterocylic ketone; which comprises in a final step:

(a) the cyclization of a compound of formula (3):

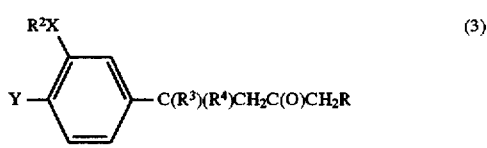

(3)

where $R^3$ is a hydrogen atom or a hydroxyl group and R is carboxyl (—$CO_2H$) or a reactive derivative thereof or a nitrile (—CN) or an imino salt, to yield a compound of formula (1) wherein $R^3$ is a hydrogen atom or a hydroxyl group and $R^6$ and $R^7$ are hydrogen atoms; or (b) the alkylation of a compound of formula (8);

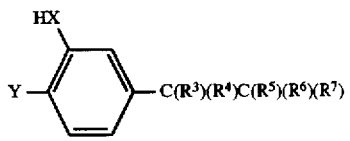
(8)

using a reagent $R^2L$, where L is a leaving group; or (c) the displacement of a halogen atom form a compound of formula (1) wherein $R^5$ is a 2-halopyridine group, to yield a corresponding compound of formula (1) wherein $R^5$ is a pyrid-2-one group; or (d) the interconversion of a compound of formula (1) to another compound of formula (1); or (e) by reaction of a compound of formula (1) with an acid or base to yield a salt of a compound of formula (1);

(f) by deprotection of a corresponding protected compound of formula (1); or (g) by resolution of a mixture of two enantiomeric forms of a compound of formula (1) to yield one enantiomeric form of a compound of formula (1).

* * * * *